US006958146B2

(12) United States Patent
Askham et al.

(10) Patent No.: US 6,958,146 B2
(45) Date of Patent: Oct. 25, 2005

(54) COMPOUNDS TO AFFECT INSECT BEHAVIOR AND TO ENHANCE INSECTICIDES

(75) Inventors: Leonard R. Askham, Pullman, WA (US); Charles F. Dunham, Spokane, WA (US); Leonard D. Felix, Jr., Olathe, CO (US)

(73) Assignee: Bug Buster Ltd., Spokane, WA (US)

( * ) Notice: Subject to any disclaimer, the term of this patent is extended or adjusted under 35 U.S.C. 154(b) by 97 days.

(21) Appl. No.: 10/447,656

(22) Filed: May 28, 2003

(65) Prior Publication Data

US 2004/0242699 A1 Dec. 2, 2004

(51) Int. Cl.$^7$ .................... A01N 37/44; A01N 37/34; A01N 37/10; A01N 37/18; A01N 65/00

(52) U.S. Cl. .................... 424/84; 424/725; 424/745; 424/DIG. 10; 514/65; 514/70; 514/72; 514/519; 514/521; 514/529; 514/530; 514/531; 514/535; 514/536; 514/537; 514/557; 514/558; 514/559; 514/560; 514/619; 514/667; 514/669; 514/918; 514/919

(58) Field of Search ................ 514/65, 70, 72, 514/519, 521, 529–531, 535–537, 557–560, 619, 667, 669, 918, 919; 424/725, 745, DIG. 10, 84

(56) References Cited

U.S. PATENT DOCUMENTS

| | | |
|---|---|---|
| 3,970,703 A | 7/1976 | Kitamura et al. |
| 4,056,610 A | 11/1977 | Barber, Jr. et al. |
| 4,195,080 A | 3/1980 | Herrera et al. |
| 4,234,567 A | 11/1980 | Flanner |
| 4,524,068 A | 6/1985 | Szejtli et al. |
| 4,548,764 A | 10/1985 | Munteanu et al. |
| 4,668,666 A | 5/1987 | Allan et al. |
| 4,888,173 A | 12/1989 | Mason et al. |
| 4,933,181 A | 6/1990 | Brown et al. |
| 4,950,682 A | 8/1990 | Pap et al. |
| 4,956,353 A | 9/1990 | Dowd |
| 4,965,070 A | 10/1990 | Messina |
| 5,043,163 A | 8/1991 | Pap et al. |
| 5,089,469 A | 2/1992 | Zampino et al. |
| 5,091,423 A | 2/1992 | Wilson et al. |
| 5,118,711 A | 6/1992 | Wilson et al. |
| 5,175,175 A | 12/1992 | Wilson et al. |
| 5,196,200 A | 3/1993 | Wilson et al. |
| 5,250,575 A | 10/1993 | Wilson et al. |
| 5,296,226 A | 3/1994 | Askham |
| 5,336,496 A | 8/1994 | Akimoto et al. |
| 5,356,881 A | 10/1994 | Verbiscar |
| 5,399,344 A | 3/1995 | Yang et al. |
| 5,401,500 A | 3/1995 | Warren et al. |
| 5,447,714 A | 9/1995 | Marin et al. |
| 5,449,695 A | 9/1995 | Marin et al. |
| 5,464,626 A | 11/1995 | Warren et al. |
| 5,466,674 A | 11/1995 | Preiser et al. |
| 5,472,701 A | 12/1995 | Warren et al. |
| 5,503,918 A | 4/1996 | Samson et al. |
| 5,521,165 A | 5/1996 | Warren et al. |
| 5,549,902 A | 8/1996 | Preiser et al. |
| 5,576,010 A | 11/1996 | Warren et al. |
| 5,633,236 A | 5/1997 | Warren et al. |
| 5,635,173 A | 6/1997 | Warren et al. |
| 5,635,174 A | 6/1997 | Warren et al. |
| 5,665,781 A | 9/1997 | Warren et al. |
| 5,693,344 A | 12/1997 | Knight et al. |
| 5,698,191 A | 12/1997 | Wiersma et al. |
| 5,744,494 A | 4/1998 | McKellar et al. |
| 5,785,982 A | 7/1998 | Warren et al. |
| 5,839,224 A | 11/1998 | Emerson et al. |
| 5,855,903 A | 1/1999 | Warren et al. |
| 5,883,112 A | 3/1999 | Pilato et al. |
| 5,900,244 A | 5/1999 | Howse |
| 5,977,029 A | 11/1999 | Fischer et al. |
| 6,010,617 A | 1/2000 | Mackerer et al. |
| 6,052,943 A | 4/2000 | Hoffmann et al. |
| 6,093,679 A | 7/2000 | Azuma et al. |
| 6,124,275 A | 9/2000 | Emerson |
| 6,143,288 A | 11/2000 | Warren et al. |
| 6,211,139 B1 | 4/2001 | Keys et al. |
| 6,242,509 B1 | 6/2001 | Berger et al. |
| 6,251,951 B1 | 6/2001 | Emerson et al. |
| 6,306,415 B1 | 10/2001 | Reifenrath |
| 6,436,439 B1 | 8/2002 | Landham et al. |

FOREIGN PATENT DOCUMENTS

| | | |
|---|---|---|
| AU | 746766 | 1/1999 |
| AU | 751583 | 7/1999 |
| EP | 0 319 757 | 4/1994 |
| EP | 0 629 344 | 10/1998 |
| EP | 0 685 995 | 7/1999 |
| WO | WO 96/08147 | 9/1994 |
| WO | WO 97/24034 | 7/1997 |
| WO | WO 97/31527 | 9/1997 |
| WO | WO 99/03345 | 1/1999 |
| WO | WO 99/46986 | 9/1999 |
| WO | WO 00/16738 | 3/2000 |
| WO | WO 00/19822 | 4/2000 |
| WO | WO 01/00020 A1 | 1/2001 |
| WO | WP 01/00026 A1 | 1/2001 |
| WO | WO 01/00032 A1 | 1/2001 |

(Continued)

OTHER PUBLICATIONS

CABA Abstract 97: 62478 (1997).*

(Continued)

*Primary Examiner*—John Pak
(74) *Attorney, Agent, or Firm*—Lee & Hayes, PLLC

(57) ABSTRACT

Various exemplary compounds, compositions and methods are disclosed. An exemplary composition includes an insecticide comprising a formula weight greater than approximately 220 and a compound comprising an insect stimulant and a formula weight less than approximately 220. An exemplary method includes applying an insecticide comprising a formula weight greater than approximately 220 and applying a compound comprising an insect stimulant and a formula weight less than approximately 220. Exemplary compounds optionally include semiochemicals of insects, plants and/or animals. Other exemplary compounds, compositions and/or methods are also disclosed.

30 Claims, No Drawings

FOREIGN PATENT DOCUMENTS

| WO | WO 01/00034 A1 | 1/2001 |
|---|---|---|
| WO | WO 01/60163 A3 | 8/2001 |
| WO | WO 01/91554 A1 | 12/2001 |
| WO | WO 01/91555 A2 | 12/2001 |
| WO | WO 02/05640 A1 | 1/2002 |

OTHER PUBLICATIONS

Chemical Abstracts 133: 292317 (2000).*

The Merck Index, Merck & Co., Inc., Whitehouse Station, NJ, 12$^{th}$ ed., 1996, p. 1369, entry nos. 8148 and 8150.*

Website at http://www.kuleuven.ac.be/bio/ento/cooper.htm, "Cooperation in insect societies—chemical communication," Copyright 1999, Katholieke Universiteit Leuven, printed Sep. 8, 2003, 3 pages.

Billen, Johan, et al., "Fine structure of the postpygidial gland in Aenictus army ants," Acta Zoologica (Stockholm) 80: 307–310 (Oct. 1999), The Royal Swedish Academy of Sciences.

Byers, J.A., "Novel diffusion–dilution method for release of semiochemicals: Testing pheromone component ratios on western pine beetle," Journal of Chemical Ecology. 14:199–212, 1988.

Kirsch, Philipp, "Amazing daze: confusion brings change," Montpellier papers website at http://phero.net/lobc/montpellier/kirsch.html, pp. 1–7, printed Apr. 24, 2003.

Ruther, Joachim, et al., "Rich in phenomena–lacking in terms. A classification of kairomones," Chemoecology, Abstract vol. 12, Issue 4 (2002), 2 pages.

University of Florida, Office of Technology Licensing brochure, University of Florida seeks partner to license, "Insect Attractant/Repellent Alternatives," 2 pages, date unavailable.

Umeda, Kai et al., Abstract—"Evaluation of Methyl Anthranilate for Use as a Bird Repellent in Selected Crops," University of Arizona College of Agriculture 2001 Vegetable Report, index at: http://ag.arizona.edu/pubs/crops/az1252/, 1 page, 2001.

Jenkinson, S.E., et al., Abstract "Development of a spreading formulation using methyl anthranilate," 21st Australian Colloid and Surface Chemistry Student Conference, Morpeth, New South Wales, Australia, 1999, 1 page.

"How Repellents Work," website at http://www.scs–mall.com/repellents.htm, 3 pages, printed Sep. 9, 2003.

Website at http://www.bugpage.com/icp.html, "PBO—Liquid Synergist Concentrate," 1 page, printed Sep. 9, 2003.

Website at http://docforgey.com/knowledge/1a.html, Doc Fergey—How Repellents Work, "Knowledge Center for Bugs and Diseases," 2 pages, printed Sep. 9, 2003.

* cited by examiner

COMPOUNDS TO AFFECT INSECT BEHAVIOR AND TO ENHANCE INSECTICIDES

TECHNICAL FIELD

The subject matter disclosed herein generally relates to compounds, compositions and methods to manage insects in or on plants.

BACKGROUND

Insecticides are often used to manage insects in or on plants. Most insecticides require contacting an insect to work effectively. Where insects exist on an exposed surface of a plant, contact may be readily achieved via spraying or other delivering means. However, where insects exist at least partially in a plant (e.g., in a stem, in a leaf, in a fruit, in a seed, etc.), contacting often becomes more difficult or practically impossible. The plant, or relevant part thereof, can create a barrier that slows transport of an insecticide. Further, an insect residing at least partially in a plant, or relevant part thereof, may exist in a favorable environment where effectiveness of an insecticide is reduced. For example, if an insect resides in a seed, the seed may act as a barrier to transport and as a shelter from unfavorable environmental conditions. Under such circumstances, the insect may be exposed to the insecticide at a tolerable rate (e.g., where metabolism can break down the insecticide and thereby prevent accumulation of a fatal concentration of insecticide). Exposure at tolerable levels may lead to an increase in insect tolerance to the insecticide and hence a decrease in effectiveness of the insecticide. At worst, the insecticide can longer achieve acceptable insect kill rates. Therefore, a need exists for means to affect insect behavior in a manner that increases and/or maintains insecticide effectiveness. Various exemplary compounds, compositions and methods described herein aim to meet this need and/or other needs.

DETAILED DESCRIPTION

The following description includes the best mode presently contemplated for practicing various described implementations. This description is not to be taken in a limiting sense, but rather is made merely for the purpose of describing the general principles of the various implementations. The scope of the described implementations should be ascertained with reference to the issued claims.

Overview

Exemplary compositions and/or exemplary methods include one or more exemplary compounds that can affect insect behavior. Such compounds generally act to stimulate insects wherein the term "stimulate" includes, but is not limited to, irritate, attract, alarm and/or repel. Hence, at times, such compounds may be referred to as stimulants with stimulation subclasses such as attractant, repellant, irritant, etc. Of course, such compounds may affect other insect behavior. Further, such compounds may act as and/or be insect semiochemicals. Yet further, such compounds may act as bird repellents. As described herein, semiochemicals include, but are not limited to, pheromones, allomones, and kairomones.

An exemplary composition includes an insecticide and one or more exemplary compounds that can affect insect behavior. Another exemplary composition includes one or more exemplary compounds that can affect insect behavior and an insect mutagen, teratogen and/or other compound that can otherwise affect insect genetics. Various exemplary compositions include one or more exemplary compounds that can affect insect behavior and that can act as a bird repellent.

An exemplary method includes applying one or more exemplary compounds that can affect insect behavior to a plant and applying an insect toxin (e.g., insecticide, etc.) to the plant. Another exemplary method includes applying an exemplary composition to a plant, wherein the composition includes an insect toxin and one or more exemplary compounds that can affect insect behavior. Various exemplary methods apply an exemplary compound that can affect insect behavior and that can act as a bird repellent.

Exemplary Compounds for Affecting Insect Behavior

Exemplary compositions and/or exemplary methods include one or more compounds that can affect insect behavior. Such compounds may be stimulants that may irritate, attract, alarm and/or repel one or more insect species. Of course, such compounds may affect other insect behavior. Further, such compounds may act as and/or be insect semiochemicals. Yet further, such compounds may act as bird repellents.

Compounds that can affect insect behavior typically include saturated and unsaturated carbon-carbon bonds. Some exemplary compounds include cyclic carbon-carbon bonds. Some exemplary compounds include aromatic carbon-carbon bonds. Most exemplary compounds include at least one oxygen atom bound to at least one carbon atom. Such compounds may exist as aldehydes, alcohols, carboxylic acids, ketones, esters, ethers and/or other types of compounds. Of course, depending on pH, etc., deprotonation or protonation may occur or a compound may exist as a salt. With respect to salts, any suitable counter ion may suffice, such as, but not limited to, sodium ions, potassium ions, ammonium ions, monoethanolamine ions, diethanolamine ions, triethanolamine ions, and/or other nitrogen containing ions.

Further, exemplary compounds that exist as ions may be paired with other ionic chemical species. For example, an exemplary compound that includes an amine may serve as a counter ion to an anionic chemical species and/or to neutralize an acid.

Some exemplary compounds that can affect insect behavior (e.g., stimulate insects) exist as non-cyclic alcohols. For example, 3,7-dimethyl-2,6-octadien-1-ol (formula weight of approximately 154 and marketed as Geraniol 980™, IFF, New Jersey) includes saturated and unsaturated carbon-carbon bonds and may exist as an alcohol and 3,7-dimethyl-6-octen-1-ol (formula weight of approximately 156 and marketed as Citronellol 950™, IFF, New Jersey) includes saturated and unsaturated carbon-carbon bonds and may exist as an alcohol.

Some exemplary compounds include a six carbon aromatic ring (e.g., a benzene ring) having one or more moieties (e.g., group or chain) bound thereto. In general, such exemplary aromatic compounds include a moiety that includes at least one oxygen atom. For example, methyl anthranilate (formula weight of approximately 151 and also known as methyl 2-aminobenzoate and having isomers methyl 3-aminobenzoate, etc.) has an ester moiety and 4-pentenophenone (formula weight of approximately 160 and marketed as LAVONAX™, IFF, New Jersey) has a ketone moiety. Other exemplary compounds, such as, bisabolene (formula weight of approximately 204), include an unsaturated six carbon ring and do not include any oxygen atoms.

An example structure for the exemplary compound methyl anthranilate (e.g., methyl 2-aminobenzoate, $C_8H_9NO_2$, formula weight approx. 151) is shown below as structure 1:

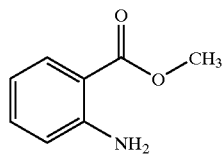

Methyl anthranilate, having an amine group, may act as a base, for example, capable of neutralizing acids.

An example structure for the exemplary compound 4-pentenophenone (e.g., 1-phenylpent-4-en-1-one, $C_{11}H_{12}O$, formula weight approx. 160) is shown below as structure 2:

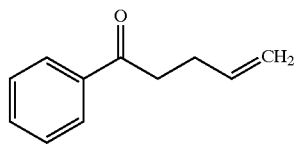

Based on the example structures 1 and 2, some exemplary compounds include a general structure given by structure 3:

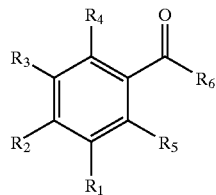

In the example structure 3, $R_1$, $R_2$, $R_3$, $R_4$, $R_5$ and $R_6$ are selected from a group that includes atoms H, N, C, and O. For example, in structure 1, $R_1$, $R_2$, $R_3$, and $R_4$, are H, —$R_5$ is N (e.g., —$NH_2$) and $R_6$ is O (e.g., —$OCH_3$), while in structure 2, $R_1$–$R_5$ are H and $R_6$ is C (e.g., —$C_4H_7$). The example structure 3 has at least seven carbon atoms and at least one oxygen atom. In a simple form, the example structure 3 is benzaldehyde, which has a formula weight of approximately 106 (e.g., $R_1$–$R_5$ are H).

Some exemplary compounds include more than one cyclic carbon ring. For example, 2-naphthaldehyde, 1,2,3,4,5,6,7,8-octahydro-8,8-dimethyl (formula weight of approximately 196 and marketed as CYCLEMONE A™ and MELAFLEU™, IFF, New Jersey) includes two adjoined cyclic carbon rings and an aldehyde moiety bound to one of the carbon rings and, the commercial product CYCLEMONE™, may include a ketone moiety bound to a carbon atom of one of the rings.

Some exemplary compounds include one or more nitrogen atoms. Such exemplary compounds may include an aromatic ring having a primary, secondary, tertiary and/or quaternary amine nitrogen atom bound to a carbon atom of the aromatic ring. For example, aminobenzene (e.g., aniline, phenylamine, etc.) includes a primary amine nitrogen atom bound to an aromatic ring, the aforementioned exemplary compound methyl anthranilate includes an amine moiety bound to an aromatic ring and another exemplary compound includes a carbon bound to a nitrogen atom of a methyl anthranilate via a carbon-nitrogen double bond wherein the carbon atom is further bound to a carbon chain (e.g., an aldimine) that includes an aromatic six carbon ring.

Other exemplary compounds having a nitrogen moiety include, but are not limited to, anthranilic acid (formula weight of approximately 137 and also known as 2-aminobenzoic acid, etc.) and p- or o-aminoacetophenone or other variants thereof (formula weight of approximately 135), which includes a ketone moiety. Referring again to the example structure 3, anthranilic acid corresponds to an $R_x$, where x is a number from 1 to 5, of N (e.g., —$NH_2$) and $R_6$ of O (e.g., —OH as a protonated acid) and p-, o-, aminoacetophenone corresponds to an $R_x$, where x is a number from 1 to 5, of N (e.g., —$NH_2$) and $R_6$ of C (e.g., —$CH_3$).

Further, an exemplary compound may include a ring wherein the ring includes a nitrogen atom. For example, methyl nicotinate (formula weight of approximately 137 and a methyl ester of nicotinic acid) includes a nitrogen atom in a ring that also includes five carbon atoms. Exemplary compounds may include methyl-N methyl anthranilate (formula weight of approximately 165), which has a secondary amine nitrogen that does not form Schiff bases with aldehydes and hence has little or no tendency to form complexes with aldehydes, etc., which may discolor or reduce efficacy (e.g., due to "sugar-amine" browning, etc.).

Another exemplary compound is methyl salicylate ($C_8H_8O_3$, formula weight of approximately 151). With respect to example structure 3, $R_x$, where x is a number from 1 to 5, is O (e.g., —OH) and $R_6$ is O (e.g, —$OCH_3$).

Various aforementioned exemplary compounds have been shown to affect insect behavior while other exemplary compounds include structural similarities and/or moieties of such exemplary compounds. Various aforementioned exemplary compounds have been shown to act as insect semiochemicals while other exemplary compounds include structural similarities and/or moieties of such exemplary compounds. Exemplary compounds include semiochemicals or analogs thereof (e.g., natural or synthetic) that may be released by insects, plants, animals, etc. Further, an exemplary compound may affect different insects differently.

In particular, various aforementioned exemplary compounds that include a nitrogen atom have been shown to affect insect behavior. For example, methyl anthranilate and methyl nicotinate are insect semiochemicals released from the postpygidial gland of worker African army ants (e.g., *Aenictinae Aenictus* sp. nova, other *Aenictus*, etc.) and o-aminoacetophenone is an insect semiochemical released from queen honey bees (e.g., *Apis mellifera* L., other *Apis*, etc.) and apparently not from worker bees. During fights, queens often release rectal fluid with a strong smell of grapes, after which they temporarily stop fighting. The fluid, which includes o-aminoacetophenone, has an effect on behavior of worker bees. In small groups, the exemplary compound o-aminoacetophone repels bees and helps to terminate agonistic interactions between queen and worker bees. The exemplary compounds methyl anthranilate and o-aminoacetophone have also been shown to exhibit repellency to birds. In general, a semiochemical is a chemical produced by an animal, an insect and/or a plant, or a synthetic analog thereof, capable of affecting insect behavior. In some examples, a semiochemical is a chemical produced by an animal, an insect and/or a plant that plays a role in ecological interactions between an insect and animals, insects and/or plants.

Exemplary compounds include semiochemicals released by insects of the aculeate or order *Hymenoptera* (e.g., sawflies, parasitic wasps, wasps, ants, and bees). Exemplary compounds from the order *Hymenoptera* include those of the genus *Apis* and genus *Aenictus*. Exemplary compounds also include compounds released by insects of the order

*Isoptera* (e.g., termites) whereas others include compounds released by insects of the orders *Homoptera* (Aphididae) and/or *Thysanoptera*. The order *Hymenoptera* includes the primary angiosperm pollinators (bees) and natural predators and parasitoids (ants, aculeate wasps, Parasitica) of other insects in many terrestrial biomes, and they have commensurate economic value in playing the same beneficial roles in crop pollination and in the control of harmful insects in agroecosystems. In general, bees can act as pollinators, not only of various crop plants, but of most of the known flowering plants.

Ants and wasps are important predators on insects, spiders and other arthropods and, less commonly, on small vertebrates. The larvae of both groups are largely, if not entirely, carnivorous. Since colony populations of some species of ants are often in excess of 50,000 larvae, it follows that considerable quantities of insect prey are collected by the foraging workers in order to feed these larvae. Hence, semiochemicals related to foraging and fighting can play an important role in survival. In particular, chemical communication via special alarm and/or attack semiochemicals can aid in insect defense and/or attack. For example, a semiochemical may deter predators and/or affect behavior of prey. Consider the exemplary compound methyl anthranilate, which deters birds and, as described in more detail below, affects behavior of insects that may be prey to *Hymenoptera* and/or *Isoptera*.

With respect to ants (e.g., *Formicidae*), *Aenictinae* includes true legionary or army ants belonging to the genus *Aenictus*. Legionary ants are known to be group raiders that do not have established nests and known to be specialized predators of other ant species. Further, colonies typically have a single queen and may number into the hundreds of thousands. The exemplary compounds methyl anthranilate and methyl nicotinate have been shown to be trail semiochemicals for *Aenictus*. Further, methyl anthranilate has been shown to trigger flight of sexuals from nest (e.g., *Camponotus* spp.).

With respect to bees, *Apis* includes honeybees (*Apis* spp., esp. *A. mellifera*). The exemplary compounds geraniol, nerol, neral, geranial, 1-heptanol, 2-phenyl-ethanol, nerolicacid, and geranolic acid have been shown to affect behavior of bees (e.g., *Panurgus banksianus, P. calacaratus*). Further, the exemplary compound 3,7-dimethyl-6-octen-1-ol (e.g., citronellol) has been shown to affect behavior (e.g., act as a territory marker) of bees (e.g., *Apidae, Psithyrus*).

Exemplary compounds that are or act as semiochemicals typically have a formula weight from approximately 80 to approximately 300. In general, such exemplary compounds are volatile. Further, such exemplary compounds typically have from approximately 5 to approximately 20 carbons. Yet further, a relationship may exist between behavior and formula weight. For example, an alarm semiochemical may require quick dispersal to be effective and hence an alarm semiochemical may be quite volatile and/or have a formula weight that is less than other types of semiochemicals. In addition, an alarm semiochemical may be ephemeral to ensure duration proportionate to alarm stimulus.

Active space typically refers to a space within which an exemplary compound concentration is above a threshold level capable of affecting insect behavior, which is sometimes referred to as a response threshold level. Achieving at least a threshold level, maintaining at least a threshold level and/or reducing to below a threshold level may depend on volatility, evaporation, diffusion, etc., of an exemplary compound. Active space may be defined with respect to a ratio of molecules released per unit time to a response threshold level in terms of molecules per unit volume. This ratio may vary depending on target behavior. For example, a sex semiochemical may have a high ratio (e.g., due to a high release rate), an alarm semiochemical may have a lesser ratio and a trail semiochemical may have an even lesser ratio (e.g., due to a lower release rate). In general, release rate, duration of release and frequency of release determine semiochemical reserve and/or semiochemical production requirements.

Various aforementioned exemplary compounds may correspond to plant semiochemicals. For example, methyl anthranilate occurs in concord grapes and geraniol occurs in citrus plants, lemon grass, roses and palmarosa. Other plant semiochemicals include nerol, lavender absolute, jasmine absolute, and racemic borneol from *Dryobalanops aromatica* (e.g., optionally produced synthetically). Yet other plant semiochemicals include benzoin (also known as benzoylphenylcarbinol $C_{14}H_{12}O_2$, formula weight approximately 212), dimethyl benzyl carbinol ($C_{10}H_{14}O$, formula weight approximately 151), carbonyl acetate, d-limonene ($C_{10}H_{16}$, formula weight approximately 136) and dihydrolinalool ($C_{10}H_{20}O$, formula weight approximately 156).

Other exemplary compounds include dimethyl substituted oxy methyl cyclohexane, oxymethyl cyclohexane, propylidene phthalide, tridecene-2-nitrile, and methyl 2-pyrrolidone-5-carboxylate. For example, 2-undecyl acetate has been shown to be a mosquito attractant, ethyl ester of 2-methyl-3-pentenoic acid has been shown to be a house fly attractant and bisabolene has been shown to be a house fly repellent, alpha-terpineol has been shown to be a sand fly attractant and dimethyl substituted oxymethyl cyclohexene has been shown to be at least a black fly and mosquito attractant.

It has been shown that beneficial insects, such as *Deraeocoris brevis* (Uhler) and *Orius tristicolor* (White) may be attracted to (E)-3-hexenyl acetate on sticky cards. In addition it has been shown that *Geocoris pallens* Stal. and hover flies (Syrphidae) were attracted to methyl salicylate baited cards. *Stethorus penctum* picipes (Casey) was attracted to the exemplary compound methyl salicylate, which has also been demonstrated to attract green lacewing (*Chrysopa nigricornis* Bermeister). It has also been shown that *Thrips hawaiiensis, T coloratus* and *Ceranisus menes* are attracted to the exemplary compound methyl anthranilate. Moreover it has been shown that the exemplary compound methyl anthranilate did not attract a closely related *T. tabaci* species. It has also been shown that methyl anthranilate is also attractive to *Thaumatomyia glabra* (Meigen) flies.

An exemplary compound may affect two different insect species differently. For example, such a compound may attract a beneficial species and repel a detrimental species. In another example, one or more of exemplary compounds may attract beneficial insects to a plant, animal structure or space to prey upon detrimental insects. In this example, the detrimental insects are controlled without the use of an insecticide. In another example, one or more exemplary compounds are used to repel beneficial insects to prevent mortality of the beneficial insects due to application of an insecticide. In such an example, an exemplary compound might be combined with an insecticide wherein the exemplary compound keeps the beneficial insects away from the insecticide that is being used to control certain pest species insects. Of course, such an exemplary compound may be applied prior to the insecticide to drive the beneficial insects out of the plants, animals, structures or spaces prior to the application of an insecticide where they may be harmed by its presence.

Exemplary Compositions

An exemplary composition includes one or more exemplary compounds that can affect insect behavior and an insecticide. Another exemplary composition includes one or more compounds that can affect insect behavior and an insect mutagen, teratogen and/or other compound that can affect insect genetics. Various exemplary compositions include one or more compounds that can affect insect behavior and that can act as a bird repellent.

An exemplary composition includes an exemplary compound and a pyrethrin and/or a pyrethroid insect toxin. For example, an exemplary composition includes an exemplary compound and lambda-cyhalothrin (marketed as WARRIOR®, Syngenta, Willmington, Del.). Over the years, semisynthetic derivatives of the chrysanthemumic acids have been developed as insecticides and are referred to generally as pyrethroids. Pyrethroids tend to be more effective than natural pyrethrins while they are less toxic to mammals. A common synthetic pyrethroid is allethrin. As described herein, the term "pyrethrins" refers to the natural insecticides derived from, for example, chrysanthemum flowers; the term "pyrethroids" refers to synthetic chemical analogs thereof, and the term "pyrethrum" is a general name covering both pyrethrins and pyrethroids. In general, pyrethroids have formula weights in a range from approximately 316 to approximately 374, the range optionally due to differences in types and amounts of esters in a pyrethrum mixture.

Another exemplary composition includes an exemplary compound and esfenvalerate (marketed as ASANA®), E.I. du Pont de Nemours and Co., Delaware). Esfenvalerate, also known as (+)Alpha-cyano-3-phenoxybenzyl-(+)-alpha-(4-chlorophenyl)isovalerate, has a formula weight of approximately 420, includes three aromatic six carbon rings and has a water solubility of less than approximately 0.3 mg/L at approximately 25° C.

Insecticides that may be suitable for use in an exemplary composition include malathion (e.g., also known as S-1,2-bis(ethoxycarbonyl)ethyl O,O-dimethylphosphorodithioate, $C_{10}H_{19}O_6PS_2$, formula weight approximately 330); dimethoate (e.g., also known as O,O-dimetyl S-methylcarbamoylmethylphosphorodithioate, $C_5H_{12}NO_3PS_2$, formula weight approximately 229); O,O-dimethyl O-(2,4,5-trichlorophenyl)-phosphoro-thioate ($C_8H_8Cl_3O_3PS$, formula weight approximately 322); zeta-cypermethrin (e.g., also known as S-cyano(3-phenoxyphenyl)methyl (+/−)-cis/trans-3-(2,2-dichloethenyl)-2,2-dimethylcyclopropanecarboxylate, formula weight approximately 416); and bifenthrin (e.g., also known as (2-methyl-1,1-biphenyl-3-yl)-methyl-3-(2-chloro-3,3,3-trifluoro-1-propenyl)-2,2-dimethyl cyclopropanecarboxylate, formula weight of approximately 423).

An exemplary composition includes an exemplary compound having a formula weight less than approximately 300 and an insecticide having a formula weight greater than approximately 300. Such formula weights may be specific and/or average formula weights. Another exemplary composition includes an exemplary compound having a formula weight less than approximately 220 and an insecticide having a formula weight of greater than approximately 220. Yet another exemplary composition includes an exemplary compound having less than three aromatic rings and an insecticide having three aromatic rings. In general, a smaller molecule can access locations more readily than a larger molecule. For example, a relatively hydrophobic exemplary compound (e.g., insoluble or slight water solubility, especially when not a salt) may more readily access locations (e.g., in or on a plant, in or on an insect, etc.) compared to a larger, relatively hydrophobic (e.g., insoluble or slight water solubility, especially when not a salt) insecticide. Some refer to slight water solubility as a range from 0.1 percent by weight to approximately 1 percent by weight.

An exemplary composition includes an exemplary compound and an insect toxin (e.g., insecticide, etc.) wherein the exemplary compound can affect insect behavior and can act as a bird repellent. For example, methyl anthranilate and o-aminoacetophone can affect insect behavior and can act as bird repellents. Further, an exemplary composition includes methyl anthranilate and/or o-aminoacetophone and a pyrethroid insect toxin. Of course, other combinations are possible wherein one or more exemplary compounds are selected and used to form a composition that includes a pyrethroid insect toxin.

An exemplary composition includes a commercially available product marketed as BIRDSHIELD™ (Bird Shield Repellent Corp., Spokane, Wash.) having methyl anthranilate as an active ingredient and includes an insect toxin. Information disclosed in U.S. Pat. No. 5,296,226, entitled "Bird Repellent Compositions", is incorporated by reference herein.

Compositions may include other compounds to achieve stability of one or more exemplary compounds and/or insecticides. Other compounds may participate in structuring compositions (e.g., lamellar, micelles, liquid crystalline, multilamellar vesicles, etc.) and/or facilitating dispensing, dispersion, time-release, etc.

Exemplary Methods

An exemplary method includes applying one or more exemplary compounds that can affect insect behavior to a plant and applying an insect toxin to the plant. Another exemplary method includes applying one or more exemplary compounds to an animal, a structure and/or a space to affect insect behavior therein or thereon and applying an insect toxin to the same animal, structure and/or space. Yet another exemplary method includes applying an exemplary composition to a plant, an animal, a structure and/or a space (or proximate to a plant, an animal, a structure and/or a space) wherein the composition includes one or more exemplary compounds that can affect insect behavior and an insect toxin. Various exemplary methods apply an exemplary compound that can affect insect behavior and that can act as a bird repellent.

An exemplary method aims to reduce insecticide usage by applying one or more exemplary compounds and/or an exemplary composition. In general, such a method aims to reduce organic and/or inorganic insecticides usage per application wherein each application aims to control detrimental insects and/or pests of forests, agricultural crops, and/or home or garden horticulture.

Another exemplary method aims to reduce a number of insecticide applications to achieve pest control by applying one or more exemplary compounds and/or an exemplary composition. For example, such an exemplary method may aim to reduce the number of insecticide applications or treatments required during a growing season of a plant as well as in, on or around animals, structures and spaces. Another exemplary method may aim to reduce the amount of insecticide in an exemplary composition required to achieve mortality in targeted insect pest species. Yet another exemplary method may aim to reduce the detrimental effects on beneficial insects by applying an exemplary composition. Another exemplary method may aim to attract beneficial insects to plants, animals, structures and/or spaces through the use of the exemplary compounds in and of themselves to plants, animals, structures and/or spaces.

Yet another exemplary method aims to reduce a need for adhering and/or spreading agents, which are typically used with insecticides. For example, the commercially available product marketed as BIRDSHIELD™, which includes the exemplary compound methyl anthranilate, includes fatty acids and/or surfactants. Use of such a product can reduce a need for adhering and/or spreading agents, for example, in an exemplary compositions and/or an exemplary method.

Another exemplary method aims to cause insects to experience a change in environmental conditions by applying one or more exemplary compounds and/or an exemplary composition. For example, an exemplary compound may cause an insect to at least partially (e.g., including fully) exit a first environment and at least partially enter a second environment. In this example, the first environment may be in a plant (e.g., in a stem, in a leaf, in a fruit, in a seed, etc.) and the second environment may be on a plant (e.g., on a stem, on a leaf, on a fruit, on a seed, etc.). Such a change may cause an insect to become exposed to detrimental environmental conditions (e.g., sun, lower or higher temperature, humidity, wind, movement, etc.) and/or to become exposed to predators or be caused to come in contact with an insecticide or another exemplary compound. Further, such a change may be irreversible in that an insect may not or cannot return to the first environment. Where the first environment includes a readily accessible food source, the insect may become food deprived. Various reasons exist for insect avoidance of reentry, including, but not limited to, an unpleasant sensation (e.g., odor, taste, etc.) or mortality.

Yet another exemplary method aims to expose an insect to an insecticide by applying one or more exemplary compounds and/or an exemplary composition. For example, an exemplary compound may cause an insect to at least partially exit a first environment and to enter at least partially a second environment wherein the second environment includes an insecticide. In some instances, an exemplary compound may access a first environment more readily than an insecticide. In such instances, the exemplary compound causes an insect to at least partially exit the first environment and thereby become exposed to an insecticide. In some situations, the first environment may be considered a sanctuary. Also consider applying an insecticide and an exemplary compound directly to an insect food source where an insect resides at least partially in substrata of the food source. Upon exposure to the exemplary compound, the insect may emerge from the substrata and contact the insecticide. Once in contact with the insecticide, effectiveness of the insecticide (e.g., mortality rate, etc.) may be increased. Moreover, the quantity or amount of the insecticide required to cause mortality may be reduced.

EXAMPLES

Grapes and Fruit Flies

An exemplary compound, methyl anthranilate, was combined with fatty acid and used to attract insects, in particular, fruit flies (*Drosophila* spp.). This exemplary compound will also repel at least some birds. The exemplary compound attracted fruit flies.

An exemplary compound, methyl anthranilate, was combined with fatty acid and applied to a surface (e.g., a treated surface) of a sticky trap and used to attract and to trap insects, in particular, fruit flies (*Drosophilia* spp.). This exemplary compound will also repel at least some birds.

A trial compared insect attraction for an untreated surface of a sticky trap and with a treated surface of a sticky trap. In less than one minute, the treated surface was covered with insects while only a few insects covered the untreated surface. Further trials demonstrated that the entire surface did not need to be treated for the exemplary compound to attract insects to the sticky trap.

A trial noted that effectiveness of the exemplary compound methyl anthranilate may be diminished in a competitive environment. For example, grape crushing and/or fermenting may release competitive agents. Hence, an exemplary method includes applying an exemplary compound only during periods where crushing and/or fermenting do not occur or applying an increased concentration or amount of an exemplary compound during such periods.

Corn and Corn-borers

An exemplary compound, methyl anthranilate, was combined with fatty acid and applied to crop fields (again, this formulation will also repel at least some birds), contemporaneously, an insecticide having a pyrethrin, lambda cyalothrin, as an active ingredient was applied to crop fields (e.g., WARRIOR™). Within a day of treatment, corn ear worm larvae (corn ear worm (*Heliothus zea*)) littered the ground. In a trial that did not apply the exemplary compound, methyl anthranilate, and fatty acid, but did apply the insecticide, pyrethrin, corn ears were still infested with a significant number of corn ear worm larvae.

In another trial, an insecticide that included a pyrethrin, lambda cyalothrin, was applied to crop fields (e.g., WARRIOR™). In this trial limited morbidity of corn ear worm larvae was observed. Later, an exemplary compound, methyl anthranilate, combined with a fatty acid, was applied to the same crop field. Within a day, corn ear worm larvae littered the ground.

An exemplary composition included an exemplary compound, methyl anthranilate, fatty acid and an insecticide that included a pyrethrin, lambda cyalothrin, as an active ingredient (e.g., WARRIOR™). The exemplary composition was applied to crop fields. Within a day of application, corn ear larvae littered the ground.

Application at or near Beginning of a Season

An exemplary composition included an exemplary compound and an insecticide. The exemplary composition was applied to corn crops at the beginning of a growing season. At the end of the growing season, a significant improvement in efficacy of an insect control program was observed. In particular, the results indicated that a single application of an exemplary compound and/or exemplary composition was sufficient to control a certain insect species or group of insect species (e.g., compared to multiple treatments required in absence of the exemplary compound). An exemplary method includes applying an exemplary compound and/or an exemplary composition to crops at or near the beginning of a growing season. Of course, other application times may be appropriate as well. In general, such a method can reduce the number of applications of an insecticide and still achieve a desirable result.

Sunflowers

An insecticide such as ASANA™ (active ingredient esfenvalerate) is suitable for use in controlling banded sunflower moth (*Cochylis hospes*). An exemplary composition that included an exemplary compound, methyl anthranilate (e.g., BIRDSHIELD™), was applied to sunflowers. After application of the exemplary composition, sunflower heads (e.g., seed containing portion of a sunflower plant) were observed for sunflower seed head larvae and no significant number of seed head larvae was observed. In contrast, sunflowers that had an application of insecticide only, exhibited a significant number of seed head larvae and other insects including mites.

An insecticide, ASANA™, was applied to sunflowers. Approximately two weeks later, an exemplary compound, methyl anthranilate (e.g., BIRDSHIELD™ at 0.006%) was applied to the same sunflowers. Within a minute of application, sunflower seed head larvae began to appear on the surface of the sunflowers. The larvae exhibited behavior that included wiggling and squirming. This behavior caused the larvae to fall off of the flower portions of the sunflowers. In addition, the exemplary compound affected behavior of other insects on the treated sunflowers. For example, insects such as mites and spiders were observed to appear from spaces between maturing seeds and to subsequently fall off the flower portion of the sunflowers.

Comparison to DEET

An exemplary composition was compared to N,N-Diethyl-m-toluamide (DEET). The exemplary composition included an exemplary compound, methyl anthranilate (e.g., BIRDSHIELD™ at 0.006% methyl anthranilate), and an insecticide, esfenvalerate (e.g., ASANA™). A 24% DEET solution is often used in a standard evaluation process by entomologists for evaluating seed weevil (*Smicronyx* spp.) infestations. In trials, the exemplary composition was observed to be as effective as the 24% DEET. No insects were observed in sunflowers seed heads sprayed with the exemplary composition or the 24% solution of (DEET).

Trials with an Exemplary Compound

Trials involved applying an exemplary compound to larvae in a laboratory growing medium. Trials demonstrated that the exemplary compound affected insect behavior.

An exemplary compound, methyl anthranilate (e.g., BIRDSHIELD™) was applied to insects that were first allowed to adapt to a laboratory environment. A control group of insects were not exposed to the exemplary compound. Observations indicated that those in the control group remained in their laboratory growing medium while those exposed to the exemplary compound emerged quickly from the laboratory growing medium and began wiggling about.

Colonies of house flies (*Drosophila melanogater*) were selected for subsequent placement in covered Petri dishes wherein each Petri dish was divided into three sections. One of the sections, a center section, was used as a control. An exemplary compound, methyl anthranilate (e.g., BIRDSHIELD™ at 0.006%) was applied to a piece of filter paper and placed in a first section while an organic solvent (e.g., deionized water), was applied to another piece of filter paper and placed in second section. Flies were then released into the center control section and lids were placed on the Petri dishes. Within one hour observations indicated that the flies avoided the section treated with the exemplary compound, methyl anthranilate, and preferred to reside in the solvent section.

More specifically, 100 captive flies were used and the sections were approximately equal in size, e.g., 33% of total space per section. Flies were released into the neutral zone of each Petri dish and monitored after 15 minutes and one hour. The results indicate that the flies avoided the treated areas at concentrations of approximately 0.25% and approximately 0.025%, while the response of the flies to the treated areas was somewhat neutral at concentrations of approximately 0.0025% and relatively neutral at approximately 0.00025%. The results demonstrate that the exemplary compound methyl anthranilate has stimulating properties which cause insects to move from one area to another.

Trapping (e.g., Stick Trap Analog)

Trials were performed using an exemplary compound as part of a trapping device (e.g., a glue coated cardboard surface). Five traps were each treated with a 1 ml solution of 0.0156%, 0.03125%, 0.0625%, 0.125% and 0.25% methyl anthranilate, respectively. The treated traps were then placed at relatively random locations in a field. An untreated trap was placed adjacent to each treated trap and the number of insects adhered to each trap recorded as a function of time. Table 1 lists the results of this trial.

TABLE 1

Exemplary compound, methyl anthranilate.

| Percent Concentration | 1 min. | 5 min | 10 min | 20 min |
|---|---|---|---|---|
| 0.0156 | 3 | 22 | 75 | >75 |
| 0.0313 | 5 | 15 | 68 | >68 |
| 0.0625 | 7 | 35 | 128 | >128 |
| 0.1250 | 15 | 62 | 256 | >256 |
| 0.2500 | 43 | 84 | 346 | >346 |
| Untreated Trap No. | | | | |
| 1 | 0 | 0 | 0 | 0 |
| 2 | 0 | 0 | 0 | 0 |
| 3 | 0 | 1 | 1 | 1 |
| 4 | 0 | 0 | 0 | 0 |
| 5 | 0 | 0 | 0 | 0 |

An exemplary compound, methyl anthranilate (e.g. Bird Shield™) was applied at 0.025% concentration to a three foot by one foot (three square feet) section of aluminum siding (treated section) and compared with a equal sized section of aluminum siding (untreated section) on the side of a building. Approximately 23 to 25 house flies (*D. melanogater*) had landed and were resting on each section. Immediately after the application of the exemplary compound to the treated section all of the flies departed. All of the flies on the untreated section remained. Thirty minutes after the application of the exemplary compound, approximately 30 flies attempted to land on the treated section within a five minute period of time but did not remain more than 6 to 8 seconds before leaving the area. Twenty-three flies remained on the adjacent untreated section. One hour after the application of the exemplary compound no flies were observed trying to land on the treated section while 15 flies remained on the untreated section. Twenty-four hours after the application of the exemplary compound no flies were observed on the treated section while 24 flies were recorded for the untreated section.

Applying Exemplary Compound After Applying Insecticide—Corn

An exemplary compound, methyl anthranilate, was applied to sweet corn after the crop had been treated with an insecticide (e.g., the pyrethrin insecticide WARRIOR™) to control corn ear worm (*Heliothus zea*). Prior to application of the exemplary compound, few if any larvae, which typically reside in the developing ear, were observed on the ground around the corn stalks. After applying the exemplary compound, methyl anthranilate, at a concentration of approximately 4.5 oz. (127 g) per acre by aircraft, a significant number of insects were observed on the ground around the corn stalks. At harvest, approximately 2% of the corn plants treated with the insecticide alone (e.g., WARRIOR™) were observed to contain ear worms while observations of the corn plants treated with the insecticide (e.g., WARRIOR™) and the exemplary compound, methyl anthranilate, indicated that they did not contain any significant number of worms in the corn ears.

Applying an Exemplary Composition—Corn

An exemplary composition included an insecticide (e.g., the pyrethrin insecticide WARRIOR™) and an exemplary compound, methyl anthranilate. An exemplary method included applying the exemplary composition at a rate of approximately 4.5 oz. (127 g) of the exemplary compound per acre to sweet corn. Twenty-four hours after the application of the exemplary composition, the ground around the corn stalks was found to be littered with dead corn ear worm larvae. No corn ear worm larvae were found in the ears of corn treated with the exemplary composition. Corn that had not been treated with the exemplary composition contained one to five corn ear worm larvae per ear of corn, even after treatment with the insecticide (e.g., the pyrethrin insecticide WARRIOR™) alone.

Applying an Exemplary Composition—Sunflowers

An exemplary composition included an insecticide (e.g., the pyrethrin insecticide WARRIOR™) and an exemplary compound, methyl anthranilate. An exemplary method included applying the exemplary composition at a rate of approximately 4.5 oz. (127 g) of the exemplary compound per acre to sunflowers in an effort to control banded sunflower moth (*Cochylis hospes*). Twenty-four hours after the application of the exemplary composition, the ground around the treated sunflowers was found to be littered with dead sunflower moth larvae. No banded sunflower moth larvae were found in the flowers treated with the exemplary composition, even seven days post-treatment. Sunflowers that had not been treated with the exemplary composition contained a significant number of (e.g., numerous) banded sunflower moth larvae, even after treatment with the insecticide (e.g., the pyrethrin insecticide WARRIOR™) alone.

Exemplary Comparison to DEET—Sunflowers

An exemplary compound, methyl anthranilate, was combined with long chain fatty acids and, in a trial, effectiveness of the mixture was compared to that of N,N-Diethyl-m-toluamide (DEET, which has a formula weight of approximately 191 and a water solubility of approximately 912 mg/L at 25° C.). DEET is often used by entomologists in standard procedures to draw sunflower seed weevils (*Smicronyx* spp.) out of the heads of sunflowers. In this trial, DEET was provided in the commercially available product DEEP WOODS OFF™ repellent (S. C. Johnson and Son's, Racine, Wis.), which has approximately 28.5% active ingredient; 1.5% other isomers and 70% inert ingredients. Forty-two flowers were randomly selected from interiors of three fields. One-half of the flowers were sprayed with the DEET containing repellent while the remaining flowers were sprayed with the exemplary compound at a concentration of approximately 0.00312% methyl anthranilate, which was combined with long chained fatty acids. The number of sunflower weevils was recorded. The results are presented in Table 2 and indicate that the exemplary compound, methyl anthranilate, was generally more effective than DEET, given the aforementioned conditions.

TABLE 2

Comparison to DEET product.

| | DEET Number of insects | Methyl Anthranilate Number of insects |
|---|---|---|
| Field No. 1 Flower No. | | |
| 1 | 5 | 8 |
| 2 | 8 | 6 |
| 3 | 6 | 0 |
| 4 | 4 | 1 |
| 5 | 3 | 2 |
| 6 | 0 | 6 |
| 7 | 1 | 5 |
| 8 | 6 | 17 |
| 9 | 5 | 16 |
| 10 | 3 | 7 |
| | Total 44; Mean = 4.4 | Total = 68; Mean 6.8 |
| Field No. 2 Flower No. | | |
| 1 | 7 | 23 |
| 2 | 18 | 24 |
| 3 | 12 | 26 |
| | Total = 37; Mean = 12 | Total = 72; Mean = 24 |
| Field No. 3 Flower No. | | |
| 1 | 19 | 11 |
| 2 | 11 | 14 |
| 3 | 6 | 10 |
| 4 | 7 | 8 |
| 5 | 4 | 4 |
| 6 | 16 | 9 |
| 7 | 9 | 7 |
| 8 | 14 | 4 |
| | Total = 86; Mean = 10.3 | Total = 67; Mean = 8.4 |

Applying an Exemplary Compound—Sunflowers

An exemplary compound, methyl anthranilate, was combined with long chain fatty acids. An exemplary method applied the mixture to fifteen maturing sunflowers in the interior of two fields that were previously sprayed with an insecticide, esfenvalerate (e.g., the insecticide product ASANA™). The mixture that included the exemplary compound was applied by spraying the mixture across the head of each flower (e.g., where seeds exist). The number of striped sunflower head moth larvae and weevils, emerging from the seeds, was recorded. The results presented in Table 3 indicate that the exemplary compound as included in the mixture was not only successful in drawing striped sunflower head math larvae out of the seeds but adult weevils as well after the crop had been treated with the insecticide alone.

TABLE 3

Exemplary Compound and Sunflowers

| Field No. 1 Flower No. | Number of Moth Larvae | Number of Adult Weevils | Field No 2 Flower No. | Number of Moth Larvae | Number of Adult Weevils |
|---|---|---|---|---|---|
| 1 | 1 | 2 | 1 | 0 | 1 |
| 2 | 0 | 0 | 2 | 0 | 6 |
| 3 | 1 | 0 | 3 | 1 | 1 |
| 4 | 1 | 0 | 4 | 1 | 0 |
| 5 | 0 | 1 | 5 | 3 | 0 |

TABLE 3-continued

Exemplary Compound and Sunflowers

| Field No. 1 Flower No. | Number of | | Field No 2 Flower No. | Number of | |
|---|---|---|---|---|---|
| | Moth Larvae | Adult Weevils | | Moth Larvae | Adult Weevils |
| 6 | 0 | 0 | 6 | 0 | 0 |
| 7 | 1 | 0 | 7 | 1 | 0 |
| Total | 4 | 3 | | 6 | 8 |
| Mean | 0.57 | 0.43 | | 0.86 | 1.14 |

Applying Exemplary Compound After Exemplary Composition

An exemplary compound, methyl anthranilate, was combined with long chain fatty acids. The exemplary compound, as mixed with the fatty acids, was applied to three fields of maturing sunflowers. Each of the fields had previously been treated with an exemplary composition that included an exemplary compound, methyl anthranilate (approx. 4.5 oz per acre mixed with long chain fatty acids) and an insecticide, in this example, esfenvalerate (approx. 8 oz per acre using the insecticide product ASANA™). Ten flowers were randomly selected from the interior of each field and one-half of the seed heads were sprayed with DEET and one-half sprayed with the exemplary compound at a concentration of approximately 0.00312% methyl anthranilate, which was in a mixture that included long chain fatty acids. Spraying sprayed across the head of each flower. The number of striped sunflower head moth larvae, emerging from the seeds, was recorded. The results presented in Table 4 indicate a high level of effectiveness of the exemplary compound when applied after an exemplary composition.

TABLE 4

Exemplary Compound and Insecticide

| Flower No. | Field No. 1 Number of Larvae. | Field No. 2 Number of Larvae | Field No. 3 Number of Larvae |
|---|---|---|---|
| 1 | 0 | 0 | 0 |
| 2 | 0 | 0 | 0 |
| 3 | 0 | 0 | 0 |
| 4 | 0 | 0 | 0 |
| 5 | 0 | 0 | 0 |
| 6 | 0 | 0 | 0 |
| 7 | 0 | 0 | 0 |

Exemplary Compound—Mosquitoes

An exemplary compound, methyl anthranilate was compared in trials to determine effectiveness of the exemplary compound relative to effectiveness of N,N-Diethyl-m-toluamide (DEET, which has a formula weight of approximately 191 and a water solubility of approximately 912 mg/L at 25° C.). In these trials, DEET was provided in the commercially available product DEEP WOODS OFF™ repellent (S.C. Johnson & Son, Inc., Racine, Wis.), which has approximately 28.5% active ingredient; 1.5% other isomers and 70% inert ingredients.

In a first trial, a human subject was exposed to a mosquito (*Aedes aegyptis*) rich environment without application of the exemplary compound or DEET. Within less than one minute the subject was covered with the insects. In a second trial, the subject sprayed one unclothed arm with the exemplary compound at a rate of 0.00312% and the other unclothed arm with DEET at a concentration of 0.24%. The subject's head remained untreated. Upon returning to the test area, the subject's head was covered with the insects within one minute. No mosquitoes were found on either arm of the subject treated with either methyl anthranilate or DEET. In a third trial the subject, after removing the DEET from his/her body, reapplied the exemplary compound to unclothed arms, head and neck before returning to the test area. The subject returned to and remained in the test area for more than one hour without any of the insects landing on his/her arms, hands and head while numerous insects were observed on the clothed portions of his/her anatomy. This particular example, demonstrated that the exemplary compound methyl anthranilate was as effective as DEET and at a lower concentrations when it was used as a mosquito repellent.

What is claimed is:

1. A composition comprising:
    an insecticide;
    methyl anthranilate; and
    at least one member selected from the group consisting of monoethanolamine, diethanolamine and triethanolamine.
2. The composition of claim 1, wherein said at least one member is triethanolamine.
3. The composition of claim 1, further comprising one or more fatty acids.
4. The composition of claim 1, wherein the methyl anthranilate is an insect stimulant.
5. The composition of claim 1, wherein the methyl anthranilate is a bird repellent.
6. The composition of claim 1, wherein the insecticide comprises a formula weight greater than approximately 220.
7. The composition of claim 1, wherein the insecticide comprises a formula weight greater than approximately 300.
8. A composition comprising:
    an insecticide comprising a formula weight greater than approximately 220;
    methyl anthranilate as an insect stimulant; and
    at least one member selected from the group consisting of monoethanolamine, diethanolamine and triethanolamine.
9. A method comprising applying the composition of claim 8 to a plant.
10. A method comprising applying the composition of claim 8 to an animal.
11. A method comprising applying the composition of claim 8 to a structure.
12. A method comprising applying the composition of claim 8 to a space to control insects in the space.
13. A method comprising:
    applying an insecticide comprising a formula weight greater than approximately 220;
    applying methyl anthranilate as an insect stimulant; and
    applying at least one member selected from the group consisting of monoethanolamine, diethanolamine and triethanolamine.
14. The method of claim 13, wherein the applying methyl anthranilate precedes the applying an insecticide.
15. The method of claim 13, wherein the applying an insecticide precedes the applying methyl anthranilate.
16. The method of claim 13, wherein the applying an insecticide and the applying methyl anthranilate occur approximately simultaneously.
17. The method of claim 13, wherein the applying methyl anthranilate repels insects.
18. The method of claim 13, wherein the applying methyl anthranilate attracts insects.

19. The method of claim 13, wherein the applying methyl anthranilate applies the methyl anthranilate to a plant.

20. The method of claim 13, wherein the applying methyl anthranilate applies the methyl anthranilate to an animal.

21. The method of claim 13, wherein the applying methyl anthranilate applies the methyl anthranilate to a structure.

22. The method of claim 13, wherein the applying methyl anthranilate applies the methyl anthranilate to a space to stimulate insects therein.

23. The method of claim 13, further comprising applying one or more fatty acids.

24. The method of claim 13, wherein said at least one member is triethanolamine.

25. The method of claim 13, wherein the applying a compound applies the compound to grape plants.

26. The method of claim 25, wherein the applying does not occur during crushing of grapes of the grape plants.

27. The method of claim 25, wherein the applying does not occur during fermenting of grapes of the grape plants.

28. The method of claim 13, wherein the applying methyl anthranilate applies the methyl anthranilate to a crop.

29. The method of claim 28, wherein the crop comprises a crop selected from the group consisting of corn and sunflowers.

30. The method of claim 28, wherein the insecticide comprises an insecticide selected from the group consisting of pyrethrum insecticides and esfenvalerate insecticides.

* * * * *